(12) United States Patent
Brandmeier (10) Patent No.: US 10,441,786 B2
(45) Date of Patent: Oct. 15, 2019

(54) SYSTEM AND METHOD FOR STIMULATING A NERVE

(71) Applicant: Medtronic Xomed, Inc., Jacksonville, FL (US)

(72) Inventor: Richard Brandmeier, Lausanne (CH)

(73) Assignee: Medtronic Xomed, Inc., Jacksonville, FL (US)

( * ) Notice: Subject to any disclaimer, the term of this patent is extended or adjusted under 35 U.S.C. 154(b) by 97 days.

(21) Appl. No.: 15/498,710

(22) Filed: Apr. 27, 2017

(65) Prior Publication Data

US 2018/0311502 A1    Nov. 1, 2018

(51) Int. Cl.
| | | |
|---|---|---|
| *A61N 1/36* | (2006.01) | |
| *A61N 1/05* | (2006.01) | |
| *A61B 5/04* | (2006.01) | |
| *A61B 5/00* | (2006.01) | |
| *A61N 1/08* | (2006.01) | |
| A61B 5/0478 | (2006.01) | |
| A61N 1/04 | (2006.01) | |

(52) U.S. Cl.
CPC ...... *A61N 1/36053* (2013.01); *A61B 5/04001* (2013.01); *A61B 5/4041* (2013.01); *A61N 1/0551* (2013.01); *A61N 1/08* (2013.01); *A61N 1/36132* (2013.01); *A61B 5/0478* (2013.01); *A61B 5/6815* (2013.01); *A61B 5/6847* (2013.01); *A61N 1/0456* (2013.01); *A61N 1/3603* (2017.08); *A61N 1/36014* (2013.01); *A61N 1/36031* (2017.08); *A61N 1/36036* (2017.08)

(58) Field of Classification Search
CPC .... A61N 1/36053; A61N 1/08; A61N 1/0551; A61N 1/36132; A61N 1/0456; A61N 1/36036; A61N 1/36014; A61N 1/36031; A61N 1/3603; A61B 5/04001; A61B 5/4041; A61B 5/6815; A61B 5/6847; A61B 5/0478

See application file for complete search history.

(56) References Cited

U.S. PATENT DOCUMENTS

| | | |
|---|---|---|
| 7,856,275 B1 | 12/2010 | Paul et al. |
| 8,885,861 B2 | 11/2014 | Beck et al. |
| 9,084,550 B1 | 7/2015 | Bartol et al. |
| 9,254,383 B2 | 2/2016 | Simon et al. |

(Continued)

FOREIGN PATENT DOCUMENTS

WO    2004-000413 A2    12/2003

OTHER PUBLICATIONS

Randolph, et al. "Electrophysiologic recurrent laryngeal nerve monitoring during thyroid and parathyroid surgery: International standards guideline statement", The Laryngoscope, vol. 121, No. S1, Dec. 22, 2010, pp. S1-S16.

(Continued)

*Primary Examiner* — Amanda K Hulbert
*Assistant Examiner* — Natasha Patel
(74) *Attorney, Agent, or Firm* — Harness Dickey (57) ABSTRACT

A stimulation electrode assembly configured to be positioned relative to a patient for an operative procedure is disclosed. An evoked stimulation response may be sensed by a sensor near a portion of a subject. The evoked response may be sensed by an electrode and determined with a monitoring system.

21 Claims, 2 Drawing Sheets

(56) References Cited

U.S. PATENT DOCUMENTS

| | | |
|---|---|---|
| 9,314,611 B2 | 4/2016 | Zschaeck et al. |
| 9,358,381 B2 | 6/2016 | Simon et al. |
| 2002/0183647 A1* | 12/2002 | Gozani ................ A61B 5/0488 600/554 |
| 2006/0085049 A1* | 4/2006 | Cory .................... A61B 5/0536 607/48 |
| 2007/0150027 A1 | 6/2007 | Rogers |
| 2008/0051852 A1* | 2/2008 | Dietrich ............... A61H 39/002 607/45 |
| 2008/0249439 A1 | 10/2008 | Tracey et al. |
| 2011/0166624 A1 | 7/2011 | Dietrich et al. |
| 2011/0306861 A1 | 12/2011 | Thramann et al. |
| 2014/0276195 A1 | 9/2014 | Papay et al. |
| 2014/0324118 A1* | 10/2014 | Simon ................ A61N 1/36021 607/46 |
| 2015/0088029 A1 | 3/2015 | Wybo |
| 2015/0148878 A1 | 5/2015 | Yoo et al. |
| 2015/0241447 A1 | 8/2015 | Zitnik et al. |
| 2016/0022987 A1 | 1/2016 | Zschaeck et al. |
| 2016/0038072 A1 | 2/2016 | Brown et al. |
| 2016/0038073 A1 | 2/2016 | Brown et al. |
| 2016/0038074 A1 | 2/2016 | Brown et al. |
| 2016/0270679 A1 | 9/2016 | Mahon et al. |
| 2016/0287112 A1 | 10/2016 | McFarlin et al. |
| 2016/0287861 A1 | 10/2016 | McFarlin et al. |

OTHER PUBLICATIONS

International Search Report and Written Opinion dated Jul. 2, 2018 in corresponding International Application No. PCT/US2018/029612.

* cited by examiner

SYSTEM AND METHOD FOR STIMULATING A NERVE

FIELD

The present disclosure relates to activity monitoring, and particularly to nerve monitoring systems and methods.

BACKGROUND

This section provides background information related to the present disclosure which is not necessarily prior art.

During various procedures, such as various throat procedures or other procedures occurring near and/or adjacent to nerve fiber, a determination of nerve integrity or stimulation may be selected. Determining nerve integrity may include ensuring or monitoring stimulation activity along or through a nerve. This may include transmission of or receiving an induced signal on a nerve. In performing such integrity monitoring, an electrode or electrode containing element is connected to a nerve or nerve fiber to monitor or stimulate the nerve fiber. Monitoring of an evoked signal at a single time or over a period of time can assist in determining integrity and continuity of a nerve. Various monitoring systems include the NIM-Response® 3.0 sold by Medtronic, Inc. having a place of business in Minneapolis, Minn. The monitoring systems can include or be operated with an electrode including an APS® electrode that allows for automatic and periodic stimulation of a nerve that may be monitored by the system.

SUMMARY

This section provides a general summary of the disclosure, and is not a comprehensive disclosure of its full scope or all of its features.

A system to provide stimulation to selected nerve bundles or paths disclosed includes electrodes that are able to be coupled to a portion of a subject, such as a human patient. The electrodes may be included in modules or members that are connected to a driving system in a wired or wireless configuration. The electrodes may include an active fixation that positively connects to at least a portion of the subject, but generally in a non-invasive manner.

The active or passive fixation systems may be provided in combination with either wired or wireless stimulation systems. The wireless electrode assemblies may also be referred to as leadless and do not require a physical connection to a monitoring system. The monitoring system may include a processor that can be a general purpose processor that is able to execute instructions stored in a memory. The memory may be a physical memory that is incorporated into the monitoring system or accessed via a network. The instructions are executed by the processor to analyze the received signals to assist in determining integrity of a nerve over time. The monitoring system may further include a display device or other output for a user to view the results of the monitoring.

The stimulation electrode need not be invasive, wherein the electrode may be placed on a subject's exterior surface to stimulate a selected nerve or nerve bundle. For example, the electrode may be placed in contact with a portion of the subject's ear, such as a pinna or auricle of the subject. The electrodes may contact selected, including specific or general portions, of the subject's ear, such as a pinna or auricle.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
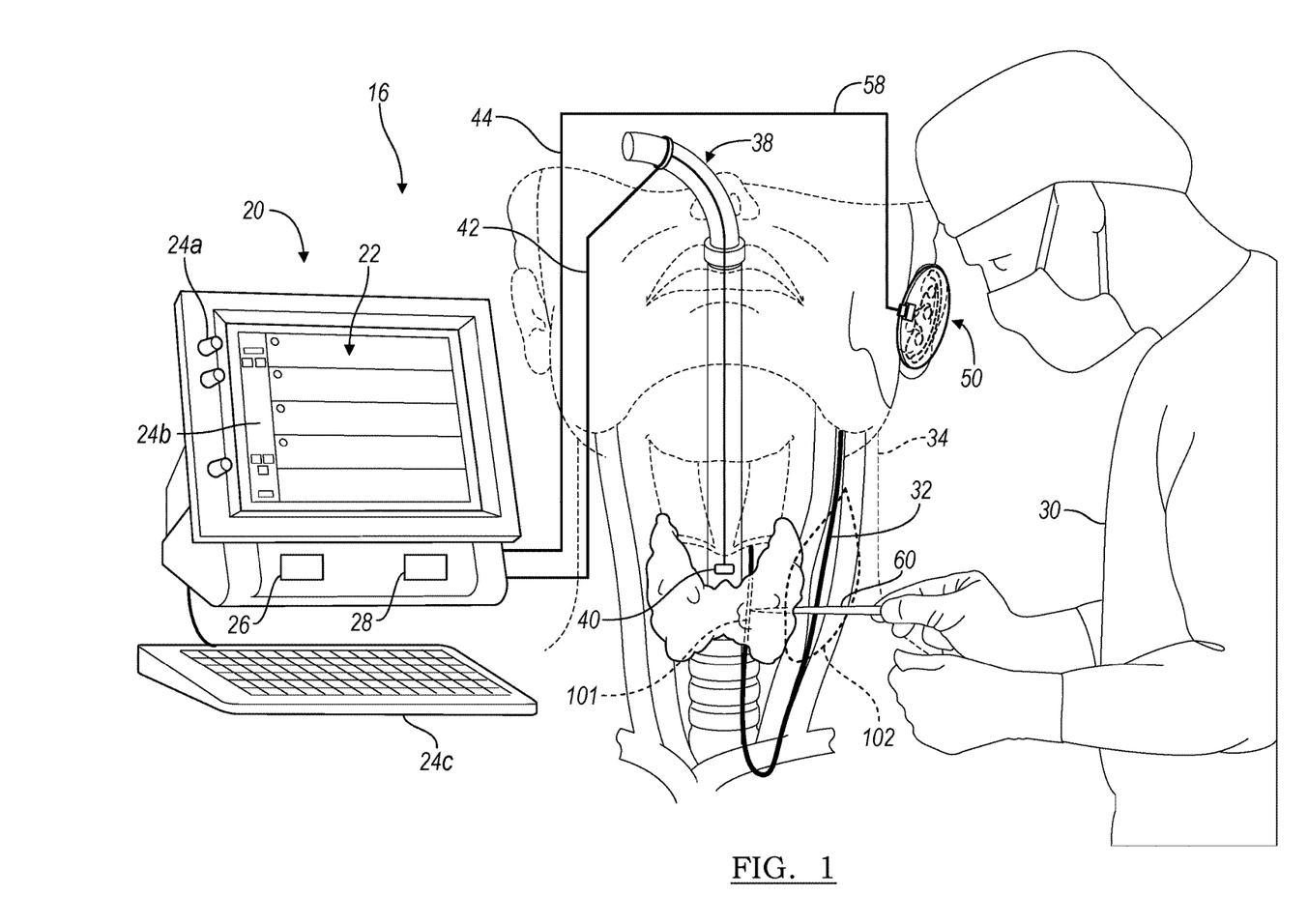
FIG. 1 is an environmental view of a monitoring system and an electrode assembly.

With initial reference to FIG. 1, a monitoring system 16, such as a NIM® nerve integrity monitoring system, may include a monitor or controller assembly 20 that has a display screen or device 22 and one or more user input devices. The monitoring system may also include monitoring systems such as those disclosed in U.S. Pat. No. 9,955,882 (U.S. patent application Ser. No. 15/252,975, filed on Aug. 31, 2016), U.S. Pat. No. 10,039,915 (U.S. patent application Ser. No. 14/678,485, filed on Apr. 3, 2015), and U.S. Pat. App. Pub. No. 2016/0287112 (U.S. patent application Ser. No. 14/678,452, filed on Apr. 3, 2015), U.S. Pat. App. Pub. No. 2016/0038072, U.S. Pat. App. Pub. No. 2016/0038073, and U.S. Pat. App. Pub. No. 2016/0038074; all incorporated herein by reference. The user input device may include one or more systems or structures to input commands of information such as knobs 24a, a touch screen 24b, a keyboard 24c, or other appropriate input devices. Input devices may also include audio or other tactile input devices.

The monitor assembly 20 may be operated as a controller for a monitoring system, and may include a processor 26 and a memory 28. It is understood that the processor 26 may access the memory 28 to execute instructions stored on the memory 28 or access other data on the memory 28. The memory 28 may include non-transitory computer accessible memory such as a physical memory, including a spinning hard disk drive, solid state memory, or other appropriate types of memory. Further, the memory 28 may not be incorporated into the monitor assembly 20, but may be accessed by processor 26, such as via a communications network. The processor 26 may be a general purpose processor that is operable to execute instructions for generating a selected output including generating a current to be delivered or injected to a subject with selected electrodes, as discussed further herein. The processor 26 may further include onboard memory. Moreover, the processor 26 may include a specific purpose processor such as an application specific integrated circuit (ASIC). Accordingly, the processor 26 may execute instructions stored on memory 28, which may be a non-transitory memory, to provide an output for display on the display device 22. A user 30 may then view the display device 22 for selected purposes, as discussed further herein.

Connected with the monitor assembly 20, may be one or more stimulation or monitoring assemblies. For example, in various procedures such as a thyroidectomy or other thyroid surgeries, monitoring a nerve 32 may be selected. The nerve 32 may include a recurrent laryngeal nerve (RLN), a vagus nerve, or other appropriate nerve, in a subject, such as a patient 34. Monitoring of the nerve, such as the vagus nerve may include a nerve monitoring esophageal tube 38, which may have one or more conductive electrodes 40 that are in contact with selected portions of the patient 34, such as a human patient. The electrode 40 may be a monitoring or sensing electrode that can be connected to the monitor system 20, via a connection 42. It is understood, however, that the connection to the monitor system 20 may also be a wireless (e.g. leadless) connection where the monitor system 20 receives a wireless transmitted signal from the electrode 40, such systems include those disclosed in U.S. Pat. App. Pub. No. 2016/0038072, U.S. Pat. App. Pub. No. 2016/0038073, and U.S. Pat. App. Pub. No. 2016/0038074; all incorporated herein by reference.

In addition, other instruments may be connected to the monitor system 20, such as electrode assemblies, including an electrode that may send or receive periodic stimulation pulses. One or more of the electrodes may include electrodes included with one or more various stimulation assemblies or stimulators 50 that may be coupled to patient 34, as discussed herein. The stimulator 50 may include a portion for holding for connecting an electrode (such as a conductive member or portion, including a metal or metal alloy) to a generator. The stimulation assembly 50 may provide a stimulation pulse to the subject 34, as discussed herein, according to selected instructions. The stimulation pulse may include an electric pulse to the subject 34. The stimulation assembly may include one or more stimulating conductors 54 (e.g. electrodes FIG. 2 and FIG. 3). The stimulation assembly 50 may be connected with a physical connection, such as a wire 58 to the monitor system 20. Again, the stimulation assembly 50 may also be wireless or leadless and not have a physical wire directly connecting the stimulation assembly 50 with the monitor assembly 20.

Other instruments may also be connected with the monitor system 20 that may be used to send or receive stimulation signals to the patient to assist in determining whether nerve interference (e.g. alteration) or damage or other tissue damage has occurred or could occur. A scalpel 60 may be manipulated by the user 30, such as a human surgeon, at a selected procedure location, such as in a throat for performing a selected procedure, such as a thyroid procedure. The scalpel 60 need not be directly connected to the monitor system 20. The monitor system 20 may be provided to monitor signals through or from the electrode assemblies 40 and 50 without requiring interactive stimulation or monitoring through the scalpel or other selected instruments performing the procedure on the patient 34. As discussed herein, according to various embodiments, electrode assemblies or stimulators may be coupled, though not directly connected (i.e. in physical contact) to one or more nerves 32 to generate a stimulation to the nerve 32 at a selected rate. The rate may be selected to account for a refractory period of the nerve. Thus, a pause or period of time between stimulations may be selected to account for the refractory period.

The operation of the monitoring system and the use of the monitoring system 16 may be similar to the NIM® monitoring system sold by Medtronic, Inc., including the NIM-Response® 3.0 nerve monitoring system. In operation, the stimulation assembly 50 may be coupled to the patient 42, as discussed further herein, and a signal may be transmitted along the connection 58 from the monitor system 20. The signal to the stimulation assembly may be generated by the monitor assembly 20 and/or with the stimulation assembly based on a signal from the monitor assembly 20. The electrode or sensor 40 may be used to receive a signal that is transmitted through the nerve 32.

The stimulation assembly 50 may be in communication with the controller system 20 to provide a selected stimulation pulse, which may be a continuous timed pules, in a manner similar to the APS® monitoring system, as discussed below. Generally, the stimulation assembly 50 may be used to transmit or deliver an electrical signal, such as with selected electrodes, to the subject 42. The stimulation may generate a current or signal that is transmitted along the nerve 32 and sensed at the electrode 40. The sensed signal may then be transmitted with the connection 42 to the control system 20. The signal transmitted to the control system 20 may be based on the signal generated with the stimulation assembly 50. The signal may change, therefore, if the nerve 32 is altered or affected and/or the signal is changed and/or the stimulation assembly is moved or adjusted relative to the subject 34.

The display device 22 may display a representation of the signal for viewing by the user 30. The signal may be determined, such as analyze a received signal and determining a portion relevant based on the input stimulation with the stimulation assembly 50. Thus, the displayed signal may be based on the stimulation provided. The sensed signal should remain unchanged as long as the input stimulation is the same and the nerve 32 relative to the input area remains unchanged or altered. Thus, as long as the signal that is displayed on the display device 22 is substantially unchanged, the user 30 may understand or conclude that the nerve 32 remains in a state similar or identical to when the monitoring began, such as intact, uninjured, or unaltered. The monitoring system 16 may allow the user 30 to perform a procedure near the nerve 32 and ensure that the nerve 32 is not damaged while monitoring the signal transmitted to the stimulation system 50.

Figure 2:
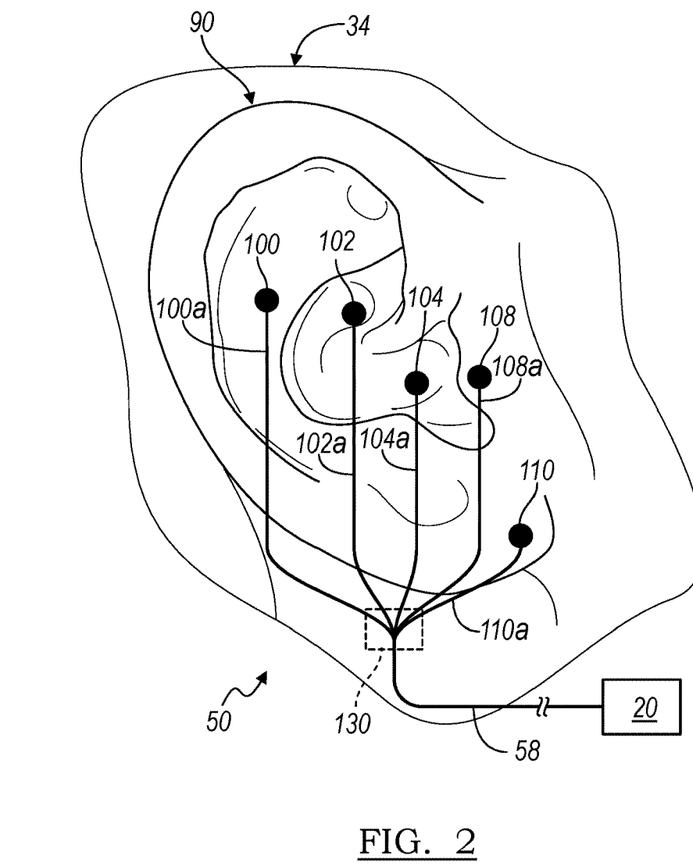
FIG. 2 is a detail environmental view of a stimulation assembly, according to various embodiments.

The continued reference to FIG. 1 and additional reference to FIG. 2, the stimulation assembly 50 may include various components. The stimulation assembly 50 may include at least one and or a plurality of contacts or electrodes, such as about five electrodes. The plurality of electrodes may include four stimulating electrodes. A first stimulating electrode 100 positioned at or on an anti-helix of an auricle portion of the subject 42. A second stimulating electrode 102 may be positioned on or at the concha cymba of the auricle 90. A third stimulating electrode 104 may be positioned on the concha cavum of the auricle 90. Further, a fourth stimulating electrode 108 may be positioned on the tragus of the auricle 90. One or more of the plurality of electrodes of the stimulation assembly 50 may include a ground or return electrode 110 may be positioned on the subject 34, which is also on the auricle 90, including at the lobule or at a portion of the helix generally spaced away from the other four electrodes 100, 102, 104, 108. In this manner, the stimulation assembly 50 may be used to drive a current through one or more of the electrodes 100, 102, 104, 108 and the ground or return electrode 110 and/or the sensor 40 may be used to create a circuit. The sensing electrode 40, however, may also receive the signal due to the stimulation carried by the nerve 32. All of the electrodes may be positioned at different and spaced apart locations on the auricle 90 or any other selected appropriate portion of the subject 34.

The auricle 90 of the subject 34 may include the portions of the anatomy, as discussed above. The auricle 90 may also include various other portions of the anatomy not specifically discussed above, but may also have electrodes positioned thereon, which may be active electrodes to deliver a current to the subject 34 or return or ground electrodes, such as the electrode 110. Nevertheless, the various portions of the auricle anatomy (discussed above) may provide a direct or high-likelihood of a current delivered along the nerve 32 of the subject 34.

As discussed above, the nerve 32 may be any appropriate nerve, such as the vagus nerve extending from the brain. The vagus nerve may be generally near a portion of the anatomy, such as within a throat that may be near or at a procedure location 101 in the subject 34. The procedure location may be accessed through an incision 102 in the subject 34. The nerve 32, therefore, may be near the instrument 60 being used to perform a procedure, such as a thyroidectomy. Ensuring that the nerve 32 remains undamaged may be assisted by providing stimulation along the nerve 32 that may be monitored with the monitoring system 20 in displaying or confirming a signal on the display device 22 for viewing by the user 30 or other appropriate individual. The signal may be based on the stimulation through the stimulation assembly 50 that is positioned at auricle 90 and the stimulation signal may be injected though the auricle 90 in an entirely (e.g. substantially only contact with an epidermis and no piercing or passing through the epidermis) and/or substantially non-invasive manner (i.e. minor or minimal piercing or breaking of the epidermis, such as to a depth of not greater than 1 millimeter (mm) below the outer surface and/or epidermis).

The electrodes 100, 102, 104, 108 may be positioned substantially on the surface or on the skin or epidermis of the subject 34. The signal may be provided through the epidermis to the nerve 32, such as using a potential at the electrodes, to provide enough power to ensure that the signal is transmitted along the nerve 32. The control system 20 may be operated to provide an appropriate potential between the electrodes 100, 102, 104, 108 and 110 to ensure that the signal is appropriately monitored by the monitoring system 20.

The electrodes 100-110 may be connected via the connection 58 to the control system 20. Thus, a signal may be transferred directly and with a physical connection to the electrodes 102-108. In addition to, or alternatively, an intermediate controller or transmission block 130 may be provided. The intermediate controller 130 may include various electronic components, such as those discussed herein. The intermediate controller 130 may include portions that allow for a wireless communication with the controller 20. Therefore, the communication 58 may not be provided as a physical connection between the intermediate controller 130 and the controller system 20. It is understood, however, that the intermediate controller 130 can also be a connection and/or splitter to allow for the single communication wire or line 58 to be plugged into or connected to a disposable portion. The disposable portion may include the intermediate controller 130 and the electrodes 100-110.

Each of the electrodes 100-110 may include respective communication lines 100a, 102a, 104a, 108a, and 110a. The individual communication lines 100a-110a may extend from the intermediate controller 130 and receive a signal through selected transmission components within the intermediate controller 130 (e.g., traces on a circuit board) from the transmission line 58 from the controller 20. The respective communication lines 100a, 102a, 104a, 108a, and 110a may allow each of the electrodes 100-110 to be placed individually and separately on the subject 34. In other words, each of the electrodes 100-110 do not have a predetermined location relative to one another and may be placed at any selected location. In various embodiments, as discussed above, however, to stimulate the vagus nerve for sensing by the sensor 40 the electrodes 100-108 each are respectively placed anti-helix, concha cymba, concha cavum, and the tragus of the auricle 90.

The controller 20, therefore, may provide signals to each of the individual electrodes 100-108 to stimulate at a selected potential and/or rate to the subject 34. This also allows each of the electrodes 100-108 to be operated substantially individually, if selected. This may also allow for frequency multiplexing and time-multiplexing. Therefore, a signal need not be provided to each of the electrodes 100-108 substantially simultaneously, but rather may happen at a selected sequence, and/or series. Further, each of the signals provided to the electrodes 100-108 to stimulate the subject 34 may be different based upon selected instructions or operation by the user 30. The control system 20 may be operated to control stimulation to the subject 34 through the respective electrodes 100-108.

The electrodes 100-110 may be coupled or held relative to the auricle 90 of the subject 34 in a selected appropriate manner. Again, as noted above, the electrodes 100-108 need not pierce or go into the epidermis of the subject 34. The electrodes 100-110 may be held to the subject 34 with an adhesive, a clamp, etc. Thus, the electrodes 100-110 may be entirely and only non-invasive.

While the electrodes 100-110 may be substantially non-invasive, to assist in holding the electrodes in a selected location, however, it is understood, a slight puncture into an epidermis may be used to assist in maintaining the electrodes 100-110 in place. The puncture may be a selected amount, such as about 0.001 mm to about 1 mm, including about 0.1 mm into the epidermis and/or dermis. The slight puncture may assist in maintaining the electrodes 100-110 at a selected location and/or assist in ensuring a transmission of the signal to the subject 34. The slight puncture may be formed with a pin or needle that extends from the electrode 100-110 and/or electrode holder. For example, a projection of about 1 mm having a diameter of 0.01 mm to about 0.2 mm having a sharp or pointed end may be used to engage the epidermis. As discussed further herein electrodes may also be incorporated into a selected member to contact the subject.

To provide the signal to the subject 34, the electrodes 100-110 may be made of a substantially conductive or electrically conductive material. Any portion that will puncture the epidermis of subject 34 may also be formed by the substantially conductive material and be in electrical contact with the electrode 100-108. Therefore, puncturing the epidermis of the subject 34 may assist in ensuring a selected current or a signal is provided to the auricle 90 for transmission along the nerve 32.

Figure 3:
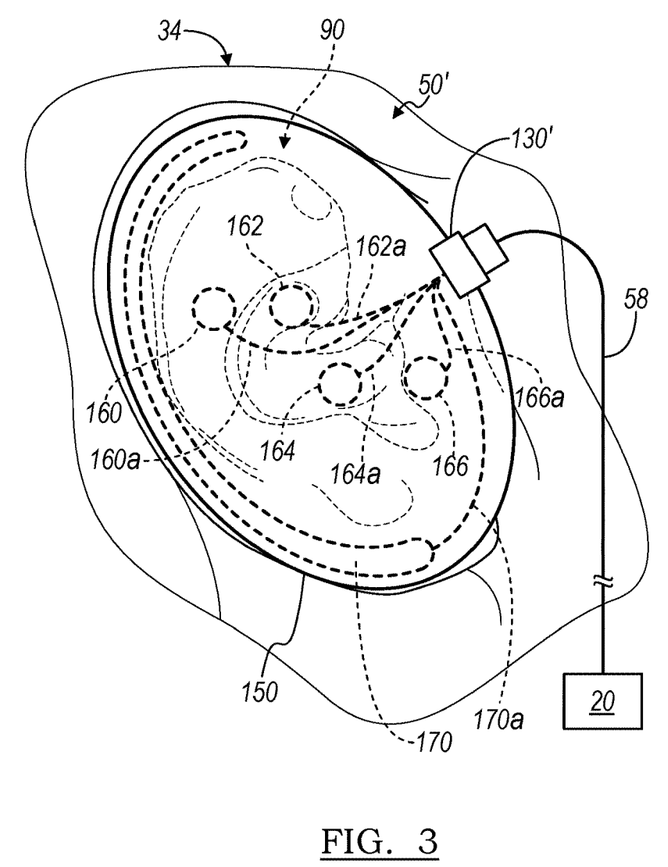
FIG. 3 is a detail environmental view of a stimulation assembly, according to various embodiments.

With continuing reference to FIG. 1 and additional reference to FIG. 3, a stimulation assembly or stimulator 50' is illustrated. The stimulation assembly 50' may be coupled to the subject 34 at or near the auricle 90 to stimulate selected portions of the auricle 90 of the subject 34 in a manner similar to the stimulation assembly 50, as discussed above. The stimulation assembly 50', however, may be formed as a single unit that may be coupled to the subject 34. The stimulation assembly may include one or more electrodes, as discussed herein, that are formed of an electrically conductive material, such as a metal or metal alloy. The electrodes may for a portion of the stimulator 50'.

In various embodiments, the stimulation assembly 50' may include a patient molded carrier or holding member 150 that has a portion that is molded to fit into the anatomy of the auricle 90, such as having portions that extend into the concha cymba and the concha cavum, and further extending to and/or into an ear canal the of the outer ear. The holding member 150 may also have portions that extend over and around the helix and lobule of the auricle 90 to assist in maintaining the stimulation assembly 50' at a selected location on the subject 34. In various embodiments, the holding member 150 may be a bespoke member that is formed based on a mold of the auricle 90 and/or precise measurements of the auricle 90. Further, the holding member 150 may be formed of a moldable material, such as a silicon or other pliable and/or tacky material that may be molded (e.g. pressed) into and onto the auricle 90 to hold electrodes at selected locations.

Further, the stimulation assembly 50' may include contact electrodes to contact various portions of the auricle similar to those discussed above. As discussed herein, the electrodes of the stimulation assembly 50' may be placed at pre-selected or predetermined locations on the holding member 150 so that they are generally not selectively position-able relative to one another. Thus, the holding member 150 may hold the electrodes relative to one another and relative to the subject 34.

The stimulation assembly 50' may include an inner surface that is configured to contact the auricle 90, and further include one or more electrode members or patches to contact portions of the auricle 90. For example, a first stimulating electrode 160 may be formed and/or placed on an inner or patient contacting surface of the holding member 150. The first stimulating electrode 160 may be made to contact the anti-helix similar to the stimulating electrode 100 discussed above. A second stimulating electrode 162 may be formed on a surface of the holding member 150 to contact the auricle 90 at the concha cymba similar to the stimulating electrode 102 discussed above. A third stimulating electrode 164 may be formed on a surface of the holding member 150 to contact the auricle 90 at the concha cavum similar to the stimulating electrode 104, discussed above. Also, a fourth stimulating electrode 166 may be formed on a surface of the holding member 150 to contact the tragus similar to the stimulating electrode 108 discussed above. It is understood, however, that any appropriate number of stimulating electrodes may be formed on the holding member 150. Further, each stimulating electrode may be formed of a plurality of contact points or portions that contact the subject 34.

Each of the electrodes 160-166 may respective or individual connections 160a, 162a, 164a, and 166a to connect to the transmission line 58. The individual connections may be formed as, for example, a thin wire connection molded into the holder 150. Further, the holder 150 may be formed to include a printed circuit board (PCB) where the individual connection 160a-166a may be formed as traces on the printed circuit board. It is understood, however, that the individual connections 160a-166a may be made to allow communication or transmission of a stimulation current to each of the electrodes 160-166 from the controller 20. In a further example, each of the individual connections 160a-166a may be connected to the intermediate controller or portion 130' similar to the intermediate controller 130 discussed above. Further, the intermediate controller 130' may include electronics and a power source to allow for a wireless communication with the controller 20 and not requiring a wired transmission line 58 between the stimulation assembly 50' and the controller 20.

Further, the stimulation assembly 50' may include a return or ground electrode 170 that may be formed on the surface of the controller 150 to be in contact with the auricle 90, such as at the helix and/or the lobule. For example, the return electrode 170 may be formed to have a global or extended contact region to contact a large area of the helix and the lobule on the auricle 90. Therefore, the return electrode 170 may be provided with a large surface area for contacting the auricle 90. Further, an individual communication line 170a may be provided in a manner similar to the individual connection lines 160a-166a. Therefore, the communication line 170a may be formed as a wire molded into the holder 150 and/or a trace on a PCB. The individual communication line 170a, however, may also be provided to be in communication with the control system 20. The sensing electrode 40, however, may also receive the signal due to the stimulation carried by the nerve 32.

Accordingly, the stimulation assembly 50' may be formed as a patient specific or fitted member either pre-procedure or intra-procedure. For example, the contacts may be positioned in a patient specific or semi-specific mold that is an inverse of the anatomy of the subject 34. The mold may be filled with a selected material (e.g. biocompatible silicone). The reverse mold may be made of the auricle 90 to form the member 150 to hold the stimulation assembly 50' in place on the subject 34. In addition, or alternatively thereto, the holding member 150 may include a pliable material that may be pushed into the auricle 90 to hold it in place during a procedure. The electrodes 160-170 may be positioned at selected locations on the member 150 and the member 150 may be pressed into the auricle 90 to hold the member 150 in place during the procedure. Regardless of the holding mechanism, however, the stimulation assembly 50' may be provided to stimulate or provide a signal to selected portions of the auricle 90 on the subject 34 and provide stimulation for monitoring by the monitoring system 20.

The holding member 150, therefore, may hold each of the electrodes 160-170 relative to one another. The holding member 150 may not allow selected and individual placement of the electrodes 160-170 on the subject. The holding member 150, however, may allow an efficient and repeatable placement of the electrodes 160-170. This may allow for an efficient and strong signal to the nerve 32.

The stimulation assembly 50, 50', according to various embodiments, may be used to stimulate the nerve 32 during a selected procedure. The stimulation of the nerve 32 may be done by providing a signal through the stimulation assembly 50, 50' to the article 90. The stimulation at the article 90 provides a signal that may be received at the electrode 40, through the nerve 32, and transferred to the monitor system 20. The received signal by the electrode 40 allows the monitor system 20 to determine a continuity of the nerve 32 from an origin to a region near the procedure location 101 and/or the incision 102. By ensuring continuity of the nerve 32, by viewing the display device 22, or other appropriate output from the monitor system 20, the user 30 may ensure that the nerve 52 is intact to the condition being monitored by the electrode 40.

The stimulation assembly 50, 50' allows for non-invasive stimulation of the nerve 32. By stimulating the nerve 32 via a transdermal signal, an incision need not be made to access the nerve 32 to contact the nerve 32 directly to monitor the integrity of the nerve 32. The stimulation assembly 50, 50', as noted above, may be placed on a surface of the epidermis of the subject 34 and a signal, such as a current, may be provided through the selected contacts or electrodes to the article 90. The signal may then be transmitted along the nerve 32 without piercing or cutting the epidermis or dermis. It is understood, as noted above, that a small piercing may be made to assist in holding the electrodes of the stimulation assemblies 50, 50' in place or to ensure greater contact with the soft tissue to increase an signal to the nerve 32, but the nerve 32 need not be accessed directly, such as with the section of the subject 34.

To stimulate selected nerves, the electrodes of the stimulator assemblies are generally placed at specific locations. As noted above, to stimulate the vagus nerve for sensing with the sensor 40, the electrodes may be placed at the specific and selected locations at noted above of the auricle 90. It is understood, however, that the contact electrodes may be positioned at other locations to stimulate other specific nerves. The nerve 32, or other appropriate nerve, may be stimulated by a surface positioning (such as only contacting and not piercing or extending into the epidermis) of a selected electrode and a selected current or signal transmitted through the contacts. The selected nerve may then be monitored with a monitoring electrode, such as the electrode 40. Thus the nerve 32, or any other appropriate nerve, may be monitored by a signal provided by the control system 20 without directly contacting the nerve 32 of an electrode. In various embodiments a stimulated EMG signal may be sensed and/or recorded with an electrode such as that included on an endotracheal tube such as the NIM TriVantrage® EMG endotracheal tube sold by Medtronic, Inc.

Further, as noted above, the stimulation assembly 50, 50' may be connected to the controller 20 via wireless or leadless system. The wireless or leadless system may include that described and disclosed in U.S. Pat. No. 9,955,882 (U.S. patent application Ser. No. 15/252,975, filed on Aug. 31, 2016), incorporated herein by reference. Generally the leadless portion may be incorporated into the stimulation assembly 50, 50', such as in the respected accessory controller 130, 130'.

The stimulation assemblies 50, 50' may be leadless electrode assemblies and need not have a direct communication with the monitor system 20. Further, the controller 20 need not directly control the leadless electrode assemblies. As discussed herein, the leadless electrode assemblies may include a controller and/or power source to automatically (i.e. upon activation) provide the stimulation pulse. The stimulation pulse may be detected by the monitor 20 to ensure that the nerve 32 is still intact. Thus, direct communication or control from the monitor 20 may not be present with the leadless electrode assemblies.

The stimulation assembly 50, 50' may provide the stimulation signal through the nerve 32, or other selected nerve, according to a predetermined frequency or program (e.g. such as a program of instructions stored with the control system 20 and/or on a controller in the electrode assembly 50, 50'). In other words, the stimulation assembly 50, 50' may provide an electrical stimulus through the subject 34 (e.g. the auricle 90) to the nerve 32 according to a selected frequency, as discussed herein. The generated or provided signal may be sensed with the sensing of receiving electrode 40 and transmitted to the control assembly 20. The stimulation assembly 50, 50' may be self-contained and can include instructions that are executed by a selected processor (such that the stimulation assembly 50, 50' may operate automatically), as discussed further herein, to stimulate or provide a signal to the nerve 32. The stimulation assembly 50, 50' may be operated in a manner similar to the APS® electrode provided with the NIM® monitoring system sold by Medtronic, Inc.

In operation, an electronics assembly may be incorporated into the stimulation assembly 50, 50' and may operate in a substantially automatic manner. It is understood that various portions may be operated with manual intervention or manual activation, but the electronics assembly may operate in a substantially automatic manner for most of the useful life of the stimulation assembly 50, 50'. In particular, a constant power may be suppled at a low current to an activation component. Upon activation of the electronics assembly a base voltage of the power supply may be stepped up for operation of the stimulation assembly 50, 50'.

A controller (which may include a processor and a selected memory including instructions for execution) included with the stimulation assembly 50, 50' may include instructions on operation of a stimulation signal to be provided with the stimulation electrodes of the respective stimulation assembly 50, 50'. The monitoring system 20 may be operated to detect the received signal, therefore, without providing the direct signal to the stimulation assembly 50, 50'. The monitoring system 20, thereafter, may display a representation of the received signal. Again, maintaining the signal so that it does not change may help ensure that no alteration of the nerve 32 has occurred during the procedure.

Example embodiments are provided so that this disclosure will be thorough, and will fully convey the scope to those who are skilled in the art. For example, activation portions, components, switches, and methods may be applied to the various electrode assemblies, as disclosed herein. The selected activation portions are not limited to any particular embodiments for any particular electrode assembly discussed herein. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of monitoring a stimulation of a selected nerve, comprising:
    contacting a first stimulation electrode at a first location to a surface of an auricle of a subject;
    contacting a second ground electrode at a second location to a surface of the auricle of the subject;
    delivering an electrical current to the subject through at least the first stimulation electrode to the subject;
    positioning a receiving electrode near the selected nerve within the subject and spaced away from the auricle; and
    operating a control system having a processor for:

receiving a signal related to the delivered current; and
displaying a representation of the received signal with a display device;
wherein the received signal is altered when the selected nerve is interrupted.

2. The method of claim 1, further comprising:
operating the control system having the processor for generating the current;
wherein the first stimulation electrode is configured to inject the current into the subject.

3. The method of claim 2, further comprising:
contacting a third stimulation electrode at a third location to the surface of the auricle of the subject;
wherein the third location is spaced apart from both the first location and the second location.

4. The method of claim 3, wherein the first stimulation electrode and the third stimulation electrode are both configured to inject the current into the subject.

5. The method of claim 3, further comprising:
connecting the first stimulation electrode, the second ground electrode, and the third stimulation electrode with a holding member shaped to fit the anatomy of the auricle; and
coupling the holding member to the auricle;
wherein the holding member positions the first stimulation electrode at the first location, the second ground electrode at the second location, and the third stimulation electrode at the third location.

6. The method of claim 1, further comprising:
performing an invasive procedure on the subject at a procedure location spaced away from the auricle.

7. The method of claim 6, wherein positioning the receiving electrode near the selected nerve within the subject includes positioning the receiving electrode near the selected nerve within the subject at or adjacent the procedure location.

8. The method of claim 4, further comprising:
contacting a fourth stimulation electrode at a fourth location to the surface of the auricle of the subject at the tragus;
contacting a fifth stimulation electrode at a fifth location to the surface of the auricle of the subject at the anti-helix;
wherein the first stimulation electrode is contacted at the concha cymba of the auricle of the subject; and
wherein the third stimulation electrode is contacted at the concha cavum of the auricle of the subject.

9. The method of claim 8, further comprising:
injecting the current into the subject simultaneously with all of the first stimulation electrode, the third stimulation electrode, the fourth stimulation electrode, and the fifth stimulation electrode.

10. A method of monitoring a stimulation of a selected nerve, comprising:
contacting a first stimulation electrode at the concha cymba of an auricle of a subject;
contacting a second stimulation electrode at the concha cavum of the auricle of the subject;
contacting a third stimulation electrode at the tragus of the auricle of the subject;
contacting a fourth stimulation electrode at the anti-helix of the auricle of the subject;
injecting a current into the subject through the first, second, third and fourth electrodes to stimulate the selected nerve;
receiving a signal related to the delivered current from the selected nerve at a sensor positioned adjacent the selected nerve and spaced away from the auricle; and
displaying a representation of the received signal with a display device.

11. The method of claim 10, further comprising:
providing a piercing member configured to extend a selected distance into the subject.

12. The method of claim 10, wherein the selected nerve includes a vagus nerve.

13. The method of claim 10, further comprising:
operating a controller to generate the current for delivering the current.

14. A system configured for monitoring a stimulation of a selected nerve, comprising:
a stimulator configured to be positioned at a first location on a surface of an auricle of a subject, the stimulator includes a plurality of electrodes configured to be positioned at a plurality of spaced apart locations on the auricle, the plurality of electrodes including at least one stimulation electrode configured to be positioned at a first location on the auricle and a ground electrode configured to be positioned at a second location on the auricle;
a sensor configured to be positioned at a third location relative to the subject and spaced away from the auricle;
a display device; and
a controller configured to:
generate an electrical signal to be delivered to the subject through at least the stimulator,
receive a signal related to the generated and delivered signal with the sensor; and
generate a representation of the received signal for display with the display device;
wherein the received signal is altered when the selected nerve is interrupted.

15. The system of claim 14, wherein the sensor is positioned at a procedure location of the subject.

16. The system of claim 14, further comprising:
a holding member having a contact surface that is shaped to fit the anatomy of the auricle and specific to a selected subject to contact at least a portion of the auricle;
wherein the holding member is configured to hold the plurality of electrodes fixed relative to one another and relative to the subject;
wherein the plurality of electrodes contact at least an anti-helix, a concha cymba, a concha cavum, and a tragus of the auricle.

17. The system of claim 16, wherein the holding member is preformed including the contact surface having a form fitting surface to contact and be held at the auricle;
wherein the plurality of electrodes are held on the contact surface to contact the auricle at least at the anti-helix, the concha cymba, the concha cavum, and the tragus of the auricle.

18. The method of claim 10, further comprising contacting a ground electrode to the auricle of the subject.

19. The method of claim 18, wherein contacting the ground electrode further includes contacting the helix and the lobule of the auricle with the ground electrode.

20. The method of claim 1, wherein the selected nerve includes a vagus nerve.

21. The system of claim 14, wherein the stimulator includes a first stimulation electrode configured to contact the concha cymba of the auricle, a second stimulation electrode configured to contact the concha cavum of the auricle, a third stimulation electrode configured to contact the tragus of the auricle, and a fourth stimulation electrode configured to contact the anti-helix of the auricle.

* * * * *